(12) United States Patent
Dennis

(10) Patent No.: US 9,066,789 B2
(45) Date of Patent: Jun. 30, 2015

(54) MULTIFUNCTION, CONTACT-PRESSURE-MANAGING ANKLE BOOTS

(71) Applicant: Michael Dennis, Scappoose, OR (US)

(72) Inventor: Michael Dennis, Scappoose, OR (US)

( * ) Notice: Subject to any disclaimer, the term of this patent is extended or adjusted under 35 U.S.C. 154(b) by 215 days.

(21) Appl. No.: 13/647,330

(22) Filed: Oct. 8, 2012

(65) Prior Publication Data

US 2013/0090586 A1     Apr. 11, 2013

Related U.S. Application Data

(60) Provisional application No. 61/545,139, filed on Oct. 8, 2011.

(51) Int. Cl.
| | | |
|---|---|---|
| *A61F 13/00* | (2006.01) | |
| *A61F 5/01* | (2006.01) | |
| *A61F 13/06* | (2006.01) | |
| *A61F 13/14* | (2006.01) | |

(52) U.S. Cl.
CPC ............. *A61F 5/0111* (2013.01); *A61F 13/061* (2013.01); *A61F 13/066* (2013.01); *A61F 13/14* (2013.01)

(58) Field of Classification Search
CPC ... A61F 5/0111; A61F 5/0127; A61F 5/0113; A61F 5/0193; A61F 13/00; A61F 13/066; A61F 13/065; A61F 13/14; A61F 13/061
USPC ........... 602/13, 65, 60–64, 79, 75, 23, 27–29, 602/53
See application file for complete search history.

(56) References Cited

U.S. PATENT DOCUMENTS

| | | | | |
|---|---|---|---|---|
| 2,858,830 | A * | 11/1958 | Robins | 604/307 |
| 6,367,106 | B1 * | 4/2002 | Gronsman | 5/709 |
| 7,455,651 | B2 * | 11/2008 | Mollica | 602/65 |
| 8,529,481 | B1 * | 9/2013 | Lois | 602/3 |
| 2010/0191163 | A1 | 7/2010 | Dennis et al. | |
| 2011/0077566 | A1 * | 3/2011 | Ganapathy | 602/13 |

\* cited by examiner

*Primary Examiner* — Kim M Lewis
(74) *Attorney, Agent, or Firm* — Mohr Intellectual Property Law Solutions, PC

(57) ABSTRACT

Apparatuses to be worn by users proximate their ankles to manage pressure and swelling, the apparatus including a wrap shaped to conform to a portion of a foot and a lower leg of the user. In some examples, the wrap defines a compressible multiple layer construction including at least one layer that including a compressible foam, a channel sized to receive a portion of the foot and the lower leg, a substantially stretchable flap sized to extend across the channel when the foot and the lower leg are positioned within the channel, a leg portion, and a foot portion, wherein the leg portion may be flexibly angled from the foot portion a bandaged area including the user's ankles. In some examples, the wrap is configured to be fitted around a portion of the user's foot and lower leg to compress at the ankle area to a selected barrier pressure.

20 Claims, 4 Drawing Sheets

MULTIFUNCTION, CONTACT-PRESSURE-MANAGING ANKLE BOOTS

CROSS REFERENCE TO RELATED APPLICATIONS

This application claims priority to copending U.S. Application Ser. No. 61/545,139, filed on Oct. 8, 2011, which is hereby incorporated by reference for all purposes.

BACKGROUND

The present disclosure relates generally to apparatuses for managing pressure on users' anatomy and/or dressing wounds and injuries, particularly in the areas around users' feet and lower legs, are described.

Medical complications arise all too often when patients must remain in relatively immobilized for long periods of time. Certain medical procedures and recovery regimens require that a patient to lie down in a relatively immobile condition for extended periods of time. Further, a patient's health and/or lack of mobility ma require that the patient lie down and remain relatively immobile for extended periods.

In some instances, the patient must rermin relatively immobilized for long periods of time with his hells down and otherwise in contact with a supporting mattress or other supporting structure. A common, dangerous, and unpleasant consequence of remaining in a position where a patient lies on his back with his heels in a relatively high-contact pressure with the underlying support structure, such as a surgical table, is decubitus injury; lying down injury. Decubitus injury, for example, decubitus ulcers, can also result when patients' heels are in extended contact with a relatively soft surface, such as a mattress when patients are bedridden.

Existing means to combat decubitus injuries include bandaging systems and manually moving patients on a regular basis. Regularly moving patients seeks to change the position of the body in contact with another surface to vary the area of the body subject to relatively high pressure. Regularly moving patients is labor intensive and is prone to human failings, such as caregivers not moving patients frequently enough and/or not being physically able to move a given patient.

Known bandaging systems are not entirely satisfactory for the range of applications in which they are employed. Many conventional bandaging systems are inadequate at properly managing the amount and distribution of anatomical contact pressure applied to bandaged areas. Not properly managing contact pressure can lead to a whole host complications, including decubitus sores, swelling, infection, improper healing of injuries and wounds, and other ailments.

Thus, there exists a need for apparatuses dressing wounds and injuries that improve upon and advance the design of known Bandaging means, particularly those that are particularly adapted for use around users' feet and lower legs. Examples of new and useful apparatuses that address these shortcomings in the field are discussed below. Further, many examples provided below include additional or alternative features augment the pressure management characteristics of described examples and/or provide supplemental functionality.

Disclosure addressing one or more of the identified existing needs is provided in the detailed description below. Examples of references relevant to apparatuses for dressing injuries include U.S. Patent References: U.S. Patent Application Publication 2010/0191163, U.S. patent application Ser. No. 13/603401, U.S. Provisional Patent Application No. 61/268,934, and U.S. Provisional Patent Application No. 61/206,127. The complete disclosures of the above patents and patent applications are herein incorporated by reference for all purposes.

SUMMARY

The present disclosure is directed to apparatuses to be worn by a user approximate his ankle for managing pressure and/or dressing wounds and injuries. Some disclosed apparatus include a wrap shaped to conform to a portion of a foot and a lower leg of the user. In some examples, the wrap defines a compressible multiple layer construction including at least one layer that including a compressible foam, a channel sized to receive a portion of the foot and the lower leg, a substantially stretchable flap sized to extend across the channel when the foot and the lower leg are positioned within the channel, a leg portion, and a foot portion, wherein the leg portion may be flexibly angled from the foot portion a bandaged area including the user's ankles. In some examples, the wrap is configured to be fitted around a portion of the users foot and lower leg to compress at the ankle area to a selected harder pressure.

DETAILED DESCRIPTION

The disclosed apparatuses will become better understood through review of the following detailed description in conjunction with the figures. The detailed description and figures provide merely examples of the various inventions described herein. Those skilled in the art will understand that the disclosed examples may he varied, modified, and altered without departing from the scope of the inventions described herein. Mane variations are contemplated for different applications and design considerations; however, for the sake of brevity, each and every contemplated variation is not individually described in the following detailed description.

Throughout the following detailed description, examples of various apparatuses are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portraital of a related feature in any given figure or example.

With reference to FIGS. 1-4, a first example of an apparatus for managing pressure on a user's anatomy and/or dressing wounds and injuries proximate the ankle of a user 90, apparatus ICC, will now be described. Applicant notes that the term dressing, applied in this context, is intended to include, at least, bandages, casts, splints, braces, or other apparatuses worn by users for recovery from injury or other therapeutic purposes.

Figure 1:
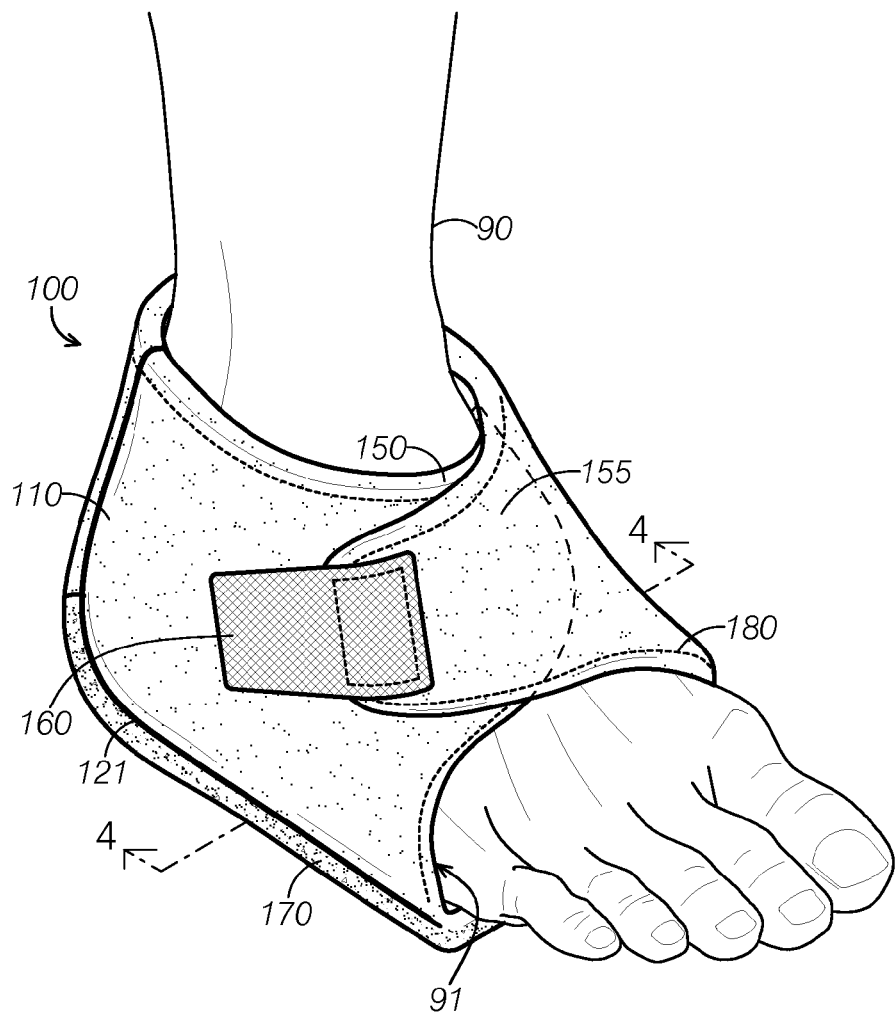
FIG. 1 is a perspective view of a first example of an apparatus for managing pressure on a user's anatomy and/or dressing wounds and injuries.

As FIG. 1 illustrates, apparatus 100 includes a wrap 110, a hook-and-pile connector component lot and an anti-skid layer 170. As FIG. 1 illustrates, apparatus 100 is configured to be secured around a bandaged area 91 of user 90, and includes several features that improve on many conventional bandages. For example, wrap 110 includes a unique multi-layered design incorporating a combination of compressible, multiple-layer layers prestressed to selected, different firmnesses. These layers of varied firmnesses provide improved pressure management characteristics compared to many conventional bandaging means. As a result, while users may often use apparatus 100 to bandage a bandaged area, many may use it for its pressure management features absent any wound or injury.

In particular, apparatus 100 may be useful for managing swelling near users' feet and legs. This may be useful, for example, after injury, after trauma, or while recovering from surgery. By better managing the pressure arising from swelling, apparatus 100 may alleviate pain, encourage proper rehabilitation, and reduce the likelihood of complications resulting from improper pressure management, such as decubitus sores.

Further, apparatus 100 includes additional or alternative features that assist attaching apparatus 100 to a user's lower leg proximate the user's foot and ankle. Further, the additional or alternative features of apparatus 100 may decrease the likelihood that users will unintentionally slip and all while wearing apparatus 100.

Figure 4:
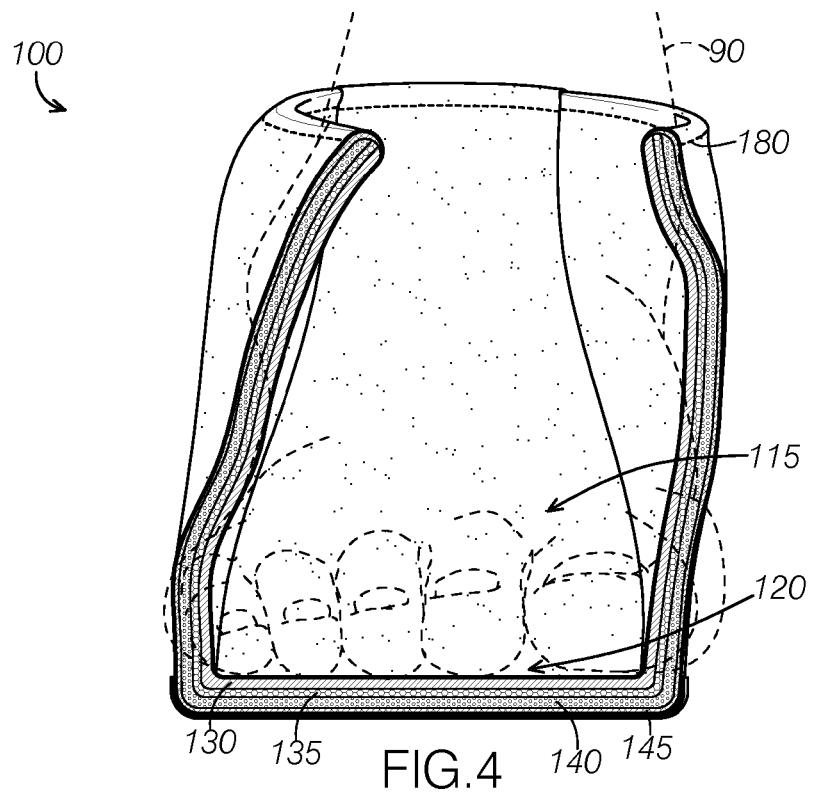
FIG. 4 is a cross-sectional view of the apparatus shown in FIG. 1 taken about the line 4-4.

As FIG. 1 illustrates, wrap 110 is shaped to conform to a portion of the foot and ankle of user 90. As shown in FIG. 1, wrap 110 contacts the ankle of user 90 within at least some portions of the interior of wrap 110. As FIG. 4 illustrates, wrap 110 defines a compressible multiple layer construction throughout substantially all of its area, defining a first layer 130, a second layer 135, a third layer 140, and a fourth layer 145. As FIG. 1 shows, wrap 110 further defines a first flap 150 acid a second flap 155.

Figure 3:
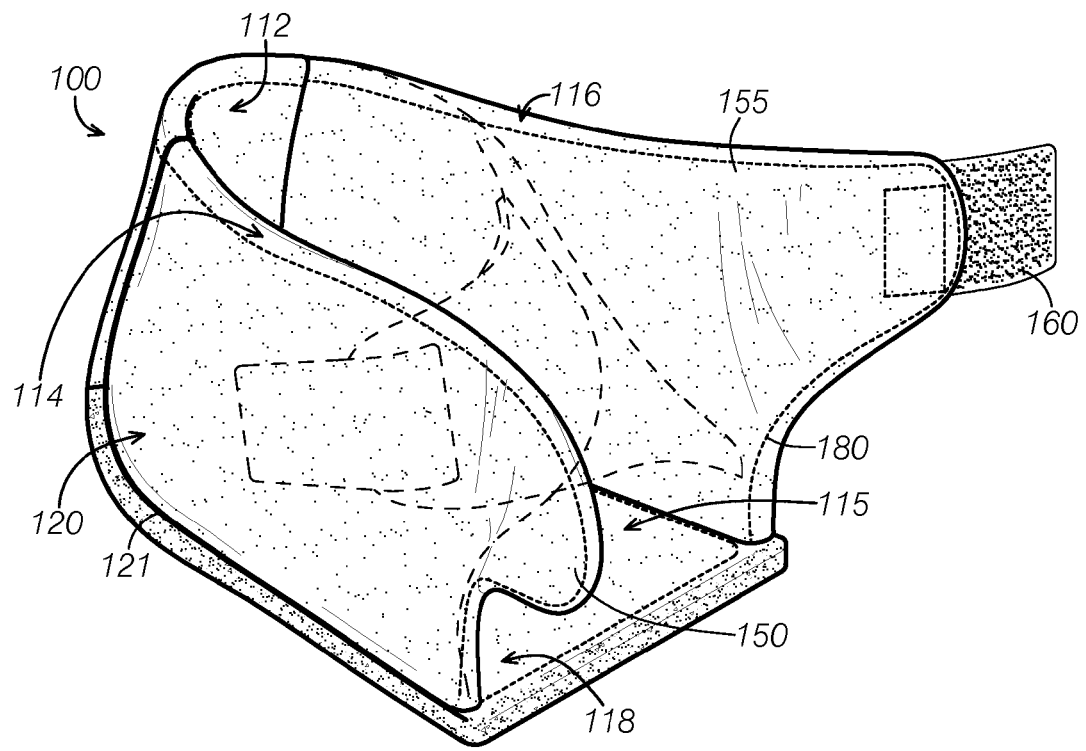
FIG. 3 is a perspective view of the apparatus shown in FIG. 1 depicting an open configuration and a closed configuration in phantom lines.

As FIG. 3 illustrates, wrap 110 extends from a leg portion 112 to a foot portion 118. FIG. 3 shows that wrap 110 further defines a first lateral edge 114 and a second lateral edge 116 extending between leg portion 112 and foot portion 118 opposite first lateral edge 114. As FIG. 3 illustrates, wrap 110 substantially defines a channel 115 routed from leg portion 112 to foot portion 118 substantially between first lateral edge 114 and second lateral edge 116. As FIG. 3 shows, 110 additionally defines a heel portion 120 substantially between leg portion 112 and foot portion 118.

As FIG. 1 illustrates, wrap 110 is configured to secure to user 90 with a portion of his foot routed through channel 115 and engaged with wrap 110. The shape of wrap 110 defines features that assist to apply substantially consistent anatomical contact pressures to the entire bandaged area in contact with wrap 110. The features of wrap 110 allow, in some contexts, wrap 110 to apply substantially consistent pressures at points of heightened anatomical contact pressure, including protruding features, such as the heels and ankles of user 90. Wrap 110 is also configured to apply substantially constant pressure to points of lesser anatomical contact pressure, such as the arch of the foot of user 90.

As FIG. 1 illustrates, wrap 110, and by extension, each of its layers, are substantially flexible, allowing wrap 110 to be wrapped around a user's foot to apply substantially even pressure around the entire bandaged area. In particular, wrap 110, when wrapped around the foot and leg of user 90, as illustrated in FIG. 1, concentrates a selected amount of pressure to either the entire bandaged area or selected areas around the leg and foot of user 90.

In some examples, wrap 110 may be secured more tightly or at various positions to adjust the distribution of pressure across regions of the foot and leg of user 90. By adjusting the tightness and position of wrap 110, for example, a user may be better able to even out the anatomical contact pressure throughout the entire bandaged area and/or concentrate or to reduce pressure at selected target areas. When a users foot and leg are routed through channel 115, leg portion 112 is configured to manage anatomical contact pressure in the area around the ankle of user 90.

As shown in 3, heel portion 120 includes a heel depression 121 configured to conform to the heel of user 90. Heel depression 121 allows wrap 110 to better manage anatomical contact pressure in that region. In some examples, the heel depression substantially evens the anatomical contact pressure proximate the user's heel to an amount that is substantially consistent with the amount of anatomical contact pressure applied to the rest of the bandaged area, As FIG. 3 shows, first flap 150 extends from first lateral edge 114 and second flap 155 extends from second lateral edge 116. Wrap 110 may be manipulated between an open configuration and a closed configuration. In the open configuration first flap 150 and second flap 155 are pulled apart from one another. In the closed configuration, first flap 150 is pulled toward second lateral edge 116 and second flap 155 is pulled toward first later aledge 114 over first flap 150. By tightening wrap 110, a user may adjust the magnitude and focus of the anatomical contact pressure applied by wrap 110.

As FIG. 3 and 4 illustrate, wrap 110 includes several features that improve how pressure is managed when properly secured. In particular, wrap 110 is compressible, due, at least partially, to its unique multi-layered construction that includes a plurality of pre-stressed compressible layers of varied firmness. This multi--layer configuration allows wrap 110 to dynamically respond to the anatomical topography of the bandaged area when attached to maintain a substantially consistent anatomical pressure across the bandaged area. Additionally or alternatively, the multi-layer configuration may apply a substantially consistent anatomical pressure despite changes in anatomical topography. Changes in anatomical topography may occur, for example, due to swelling, the patient moving, or bodily functions. Wrap 110 may dynamically respond to these changes, for example, compressing, bending, flexing elastomeric stretching, and elastomeric relaxing, particularly in the compressible, elastomeric foam layers of wrap 110.

Figure 7:
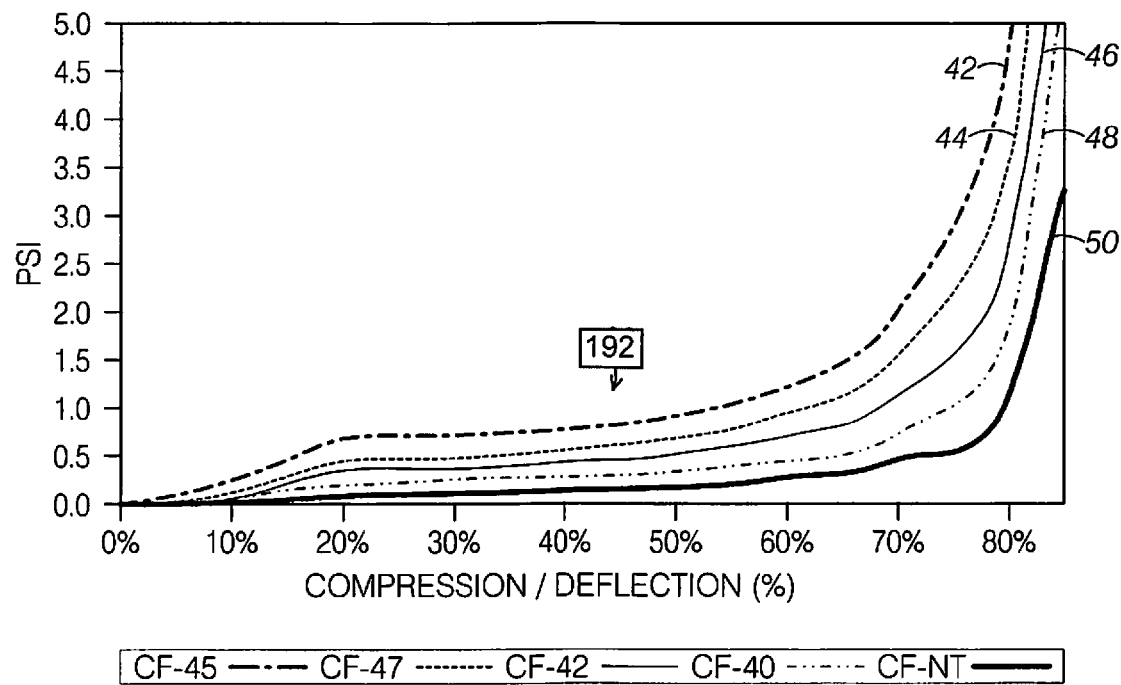
FIG. 7 is a chart depicting a plateau condition for several viscoelastic foams suitable for use in disclosed examples.

When wrap 110 is properly secured to a users foot and leg, these compressible layers are placed in a plateau condition. FIG. 7 illustrates a plateau condition 192. When the compressible layers are in this plateau condition, wrap 110 applies a substantially consistent anatomical contact pressure across the entire bandaged area even when applied to areas of the body subject to changing anatomical conditions.

The FIG. 7 chart depicts compressive-deflection vs. compression-force curves for a number of prestressed viscoelastic compressible foam materials made under the Confor® brand, including CF-45 at line 42, CF-47 at line 44, CF-42 at line 46, CF-40 at line 48, and CF-NT at line 50. As FIG. 7 illustrates, the compressive-deflection vs. compression-force curve for each of these foam materials are substantially linear in the range associated with plateau condition 192, between approximately 19% and 60% compression for each foam.

The chart illustrated in FIG. 7 shows that the associated viscoelastic compressible foam materials, even when exposed to changing anatomical conditions that vary the amount of pressure applied to the compressible layers, will apply a substantially constant amount of anatomical contact Pressure to a user. Small deviations in the anatomical contact pressure applied by wrap 110 when it remains characterized by plateau condition 192 are typically anatomically insignificant.

In some examples, the anatomical contact pressure is selected to not exceed a barrier pressure, that is a pressure representing a threshold between safe and dangerous conditions for the onset of decubitus injury. A barrier pressure of approximately 32 millimeters of mercury is generally recognized for the human anatomy. Thus, apparatus 100 is configured to target applying less than 32 millimeters of mercury of anatomical contact pressure.

Applying an appropriate amount of contact pressure may be critically important to users, particularly those who must wear apparatus 100 for a prolonged period of time in particular, applying an anatomical contact pressure that is greater than the static pressure of fluid in the bandaged area may control undesirable swelling resulting from retaining fluids in an anatomical region. Many appropriate levels of anatomical contact pressure exceed common static pressure levels of fluid in users' anatomy.

Applying too much pressure, however, may block venous blood flow returning from the bandaged area. Many appropriate levels of anatomical contact pressure fall below levels that would block venous blood flow, As a result, a pressure range between a lower threshold pressure, below which may not adequately inhibit retaining fluid, and an upper threshold pressure, above which may block venous blood flow, often defines a good target pressure range for the apparatus to apply to a patient's anatomy. Typically, changes in pressure between the lower threshold pressure and the upper threshold pressure are considered anatomically insignificant. A range of 0.3 pounds per square inch to 0.7 pounds per square inch has been found to be anatomically insignificant.

If anatomical contact pressures all outside this range, however, serious problems may arise. In many cases, these serious problems may be slow onset and difficult to detect before it is too late to take measures that are adequate to prevent serious injury, complications, or pain. Such complications may include, for example, decubitus sores or painful swelling. By increasing the consistency with which wrap 110 is able to maintain a anatomical contact pressure within an appropriate range. Accordingly, apparatus 100 significantly reduces the prevalence of medical complications that occur in conventional bandages and the like by applying appropriate levels of anatomical contact pressure.

Because wrap 110 is able to dynamically adjust to both the initial topography of the bandaged area and changes that occur while wrap 110 is secured, wrap 110 is able to apply appropriate level of anatomical contact pressure a greater percentage of time than many conventional bandaging and pressure-managing devices. When bandages or other injury/wound dressing means are initially secured, they are typically secured to apply an anatomical contact pressure in the 0.3 to 0.7 range discussed above. However, when these bandages or apparatuses remain secured for long periods of time, conditions often change and the level of anatomical contact pressure may fall out of an appropriate range. Conventional solutions often fail to maintain an appropriate pressure range when a patient moves, voluntarily or involuntarily, or when the patient experiences internal bodily movements. Further, the bandage's or apparatus's securing means may loosen over time, reducing its applied anatomical contact pressure. These changing conditions may place patients at risk even when the bandage or dressing was initially properly secured, Wrap 110's ability to remain in the plateau state characterized by plateau condition 192 when exposed to changing compressive pressures allows wrap 110 to reduce the risk of complications arising from prolonged exposure to high and variable anatomical contact pressure. Indeed, wrap 110 is able to maintain substantially consistent levels of anatomical contact pressure through many common changes in conditions when apparatus 100 is attached to a person's anatomy for extended periods, such as due to the reasons described above. The ability of apparatus 100 to apply a consistent amount of pressure in changing conditions may be particularly useful for periods of long-term recovery from surgery or serious injury. Indeed, many features of apparatus 100 allow it to apply pressure more consistently within a plateau state or apply a consistent amount of anatomical contact pressure despite changing conditions; each improvement that apparatus 100 provides in these areas defines an important way in which apparatus 100 solves the problems inherent in many conventional long-term bandaging means.

Because apparatus 100 is shaped to specifically conform to the areas of a user's foot and legs proximate the user's ankle, the pressure managing characteristics of apparatus 100 may be particularly useful for the purpose of controlling and managing swelling in the foot and/or ankle area. Controlling and managing swelling in the foot and/or ankle area may be useful, for example, as the user is recovering from surgery. Further, apparatus 100 provides multiple features that allow users significant freedom to adjust the tightness and position in which apparatus 100 is secured. Apparatus 100 may, as a result, concentrate or reduce pressure in particular target areas, in some examples, to better even anatomical contact pressure across the entire bandaged area.

In some examples, specific target areas around which apparatus 100 may specifically, target to concentrate or reduce pressure include the entire foot, the ankle, the heel, and/or one or more high-pressure anatomical contact points of a patient. Apparatus 100 may target these areas based how wrap 110 is positioned and tightened when secured to a given anatomical region of a patient. In some configurations, for example, wrap 110 may be secured to user 90 to reduce pressure at target areas around and including one or more selected typically high-pressure anatomical contact points, such as heels, to diminish the variance in pressure these high-pressure anatomical contact points cause. For example, heel depression 121 is configured to reduce the effect on the anatomical contact pressure applied by the remainder of wrap 110 distal the user's heel of the normally high contact pressure caused by the user's heel.

Some wrap examples may include additional or alternative design features that arc specifically configured to target specific target areas. Some wraps may, for example, include layers that vary in shape or thickness from the layer examples shown in FIG. 4, which are substantially uniform. For example, the relative and absolute thicknesses of each layer may be adjusted to better target different target areas. Additionally or alternatively, each layer may vary in thickness at various positions on the wrap. For example, the thickness of a relatively firm laser may be increased selected areas to apply greater pressure to the user in selected target areas. Further, additional or alternative layers of selected firmness may be used to further adjust the pressure applied by a wrap and its cushioning characteristics.

In some examples, concentrating or reducing pressure on target areas wholly separate from the high-pressure anatomical contact points may be effective in achieving a substantially consistent level of anatomical contact pressure throughout. In other examples, however, wraps may be configured to concentrate or reduce pressure to some or all high-pressure anatomical contact points, in some cases in equal or greater amount than surrounding non-hi pressure anatomical contains a areas. Applying less pressure in high-pressure areas could, for example, increase pressure elsewhere to place the entire bandaged area at an appropriate level of anatomical contact pressure. This may even be necessary, in some examples, to apply a substantially consistent pressure over the entire covered region of users feet and legs. In some examples, applying a selected amount of pressure throughout the covered portions of users' feet and legs may be required to place the entire covered area within the plateau area shown in FIG. 7.

As a result, any of apparatus 100's shape or physical design features that allow it to concentrate or reduce anatomical contact pressure in target areas furthers its ability to apply a consistent amount of pressure across the entire bandaged area, Because the shape of apparatus 100 conforms to target anatomical regions, compresses a patient's anatomy with a predetermined, target pressure range, and dynamic adjusts to changing anatomical conditions, apparatus 100 is well suited to dress users' leg and foot areas during recovery from wounds, injury, or trauma. In particular, apparatus 100 may be particularly useful in managing pain and swelling resulting from these causes. Further, apparatus 100 may reduce the incidence of complications arising from consistent application of an inappropriate level of anatomical contact pressure, such as decubitus sores or other pain or swelling. Additional or alternative applications may include wrapping and stabilizing a wound just received by a user, compression bandaging of other kinds of post-medical--treatment not necessarily related to surgery or recent wound, or wrapping or stabilizing users' feet and legs when users have brokers bones proximate the bandaged area.

As FIG. 4 illustrates, the layers of wrap 110 extend substantially across the entire area of wrap 110. The layers of wrap 110 include multiple layers, including first layer 130 proximate channel 115 and fourth layer 145 distal channel 115. As FIG. 4 shows, first layer 130 is exposed to the interior of wrap 110, substantially facing, on one side, channel 115. First layer 130, or, in some examples, an upper, anatom facing side thereof, is constructed primarily of a moisture-wicking fabric material. In some examples, this may define a medical-grade, moisture--resistant, tricot fabric. In some examples, first layer 130 may additionally or alternatively include heat, friction, and/or shear minimizing materials, throughout or on the upper, an side.

Some examples may, for instance, be constructed of a moisture-wicking fabric material throughout with a thin sub-layer of heat, friction, and/or shear minimizing material applied or bonded to the anatomy-facing side.

Each of these features may serve important functions, as first layer 130 provides the most immediate contact with the user. The moisture wicking features prevent overexposure to liquids that accumulate within the bandage that may cause, for example, infection or other complications. Such liquids may include bodily fluids, such as those released from wounds or sweat, or liquids that inadvertently enter from the exterior of apparatus 100.

Further, heat-management features may restrict or prevent the wound from overheating. Overheating may produce sweat or produce other complications and is thus undesirable. Further, the friction and/or shear minimizing materials help avoid a user's foot from sticking to first layer 130, which could reduce the ability of apparatus 100 to properly manage pressure and/or unintenionally re-open partially healed wounds.

As FIG., 4 illustrates, second layer 135 is adjacent acid interfacially engaged, throughout substantially all of its area, to first layer 130 distal channel 115. Second layer 135 includes, and in many examples is constructed primarily of a first compressible, prestressed viscoelastic foam material. In some examples, the particular foams may be of the type or substantially similar to a viscoelastic foam sold under the Confor® brand, constructed by AEARO Specialty Composites. First layer 130, specifically, is constructed primarily of the Confor® viscoelastic foam sold under the product designator CF-42. In various examples, other similar compressible viscoelastic foams, such as that sold under the product designator CF-40, may be used.

As FIG. 4 illustrates, third layer 140 is adjacent and interfacially engaged, throughout substantially all of its area, to second layer 135 distal first layer 130. Third layer 140, similar to second layer 135, is constructed largely of a second compressible, prestressed viscoelastic foam material. Similar to second layer 135, third layer 140 is constructed of a foam sold under the Confor® brand constructed by AEARO Specialty Composites, specifically CF-45. Other similar viscoelastic foams may be used, but many examples include second layers and third layers defining differential firmness between the two layers; specifically with the third layer firmer than the second. This differential firmness, particularly in, but not limited to, cases where the second, more interior layer is less firm than the third, more exterior layer, helps wrap 110 achieve a plateau condition similar to the one shown in FIG. 7.

The increased firmness of third layer 140 allows it to substantially serve as a compressible partial backstop to the more readily compressible second layer 135. As FIG. 7 illustrates, however, the Confor® foam selected for third layer 140, while firmer than the one in second layer 135, still exhibits plateau condition 192 at a similar range of compression deflection. As a result, third layer 140 will still compress if necessary to maintain an appropriate level of anatomical contact pressure, but will hold its form more consistently than second layer 135.

Pairing the differential levels of foam provides numerous benefits. For example, the softer foam makes it easier for users to more easily initially secure or adjust apparatus 100 to an appropriate level of anatomical contact pressure while the firmer foam helps maintain an appropriate level of anatomical contact pressure more consistently.

As FIG. 4 illustrates, fourth layer 145 is adjacent and interfacial/ engaged, throughout substantially all of its area, to third layer 140 on the side opposite second layer 135. As FIG. 1 shows, fourth layer 145 defines a pile material on substantially all of the exterior surface of wrap 110, the pile material being compatible with hook-and-pile connector component 160. In particular, fourth layer 145 largely consists of a pile material compatible with many hook-and-pile systems sold under the product name Veltex®. By providing the pile material compatible with hook-and-pile connector component 160, fourth layer 145 provides a wide range of areas to which second flap 155 may be pulled toward and attached. By allowing users to pull and attach second flap 155 to various positions via hook-and-pile connector component 160 and fourth layer 145, apparatus 100 provides users with a great deal of adjustability with respect to the tightness and position in which apparatus 100 is secured. As a result, users are able to adjust apparatus 100, using these features, to concentrate or reduce anatomical contact pressure at target areas around a user's leg and foot, As FIG. 3 illustrates, apparatus 100 includes hook-and-pile connector component 160 positioned on the edge of second flap 155 distal second lateral edge 116. Hook-and-pile connector component 160 may be operatively paired with the exterior of wrap 110 to secure second flap 155 in a selected position. Users may secure hook-and-pile connector component 160 to fourth layer 145 to position apparatus 100 in a closed configuration. By adjusting the position in which hook-and-pile connector component 160 is engaged with the exterior of wrap 110, wrap 110 may be adjusted to apply different pressures and/or target different areas of user 90 to concentrate or reduce the amount of applied anatomical contact pressure For example, second flap 155 may be pulled tight to secure hook--and-pile connector component 160 to wrap 110 at a position more proximate heel portion 120 to increase the amount of pressure applied substantially throughout wrap 110.

Figure 2:
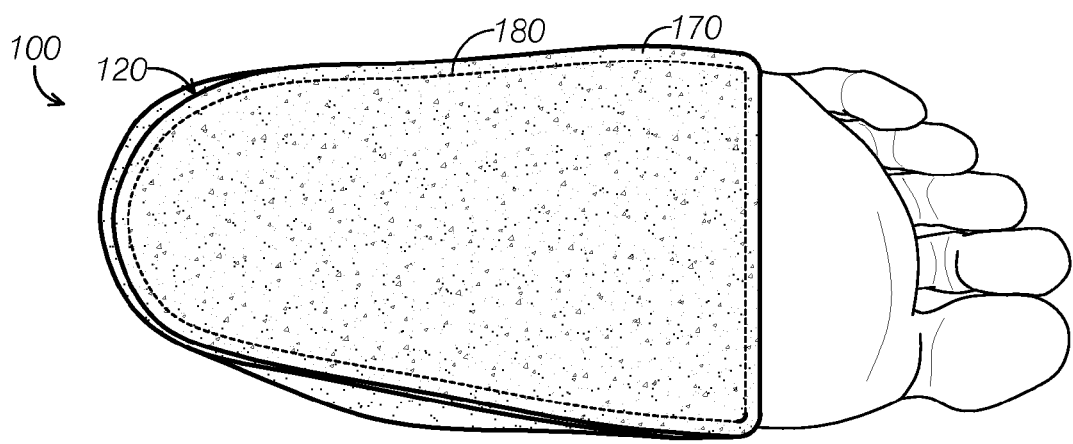
FIG. 2 is a bottom view of the apparatus shown in FIG. 1.

As FIGS. 2 and 4 illustrate, anti-skid layer 170 is attached to wrap 110 below a users foot when standing. Anti-skid layer 170 defines a base-attached patch, or layer, formed of any suitable high fiction, anti-skid material which functions to offer "sure-footed," anti-skid performances under circumstances where the person wearing apparatus 100 of the invention is walking. Anti-skid layers similar to anti-skid layer 170 may be particular important in examples including pile material on the most exterior layer of the multiple--layer wrap, as the pile material may be slippery, and therefore, may create a hazard. An anti-skid layer reduces this hazard. Indeed, an anti-skid layer may be useful for safeguarding against a user slipping whether or not the wrap exterior material is particularly prone to slipping.

As FIGS. 2 and 4 illustrate, anti-skid layer 170 is appropriately shaped for the base of apparatus 100. In some examples, anti-skid layer 170 may define a rubber, a compressible viscoelastic foam, or other suitable material.

Each layer of wrap 110, including first layer 130, second layer 135, third layer 140, fourth layer 145, and anti-skid layer 170 is held together by suitably placed stitching 180. Stitching 180, as shown in FIGS. 1-4, is routed through each layer to retain the layers interfacially bonded to adjacent layers over substantially of their area. Some examples, as described below, may additionally or alternatively interfacially bond adjacent layers using an adhesive. While an adhesive may increase the surface area of each layer that is interfacially bonded to an adjacent layer relative to stitching alone, stitching may more reliably fasten the layers together over time. As a result, each approach has unique benefits and drawbacks. Some examples may, of Course, use both stitching and an adhesive.

Figure 5:
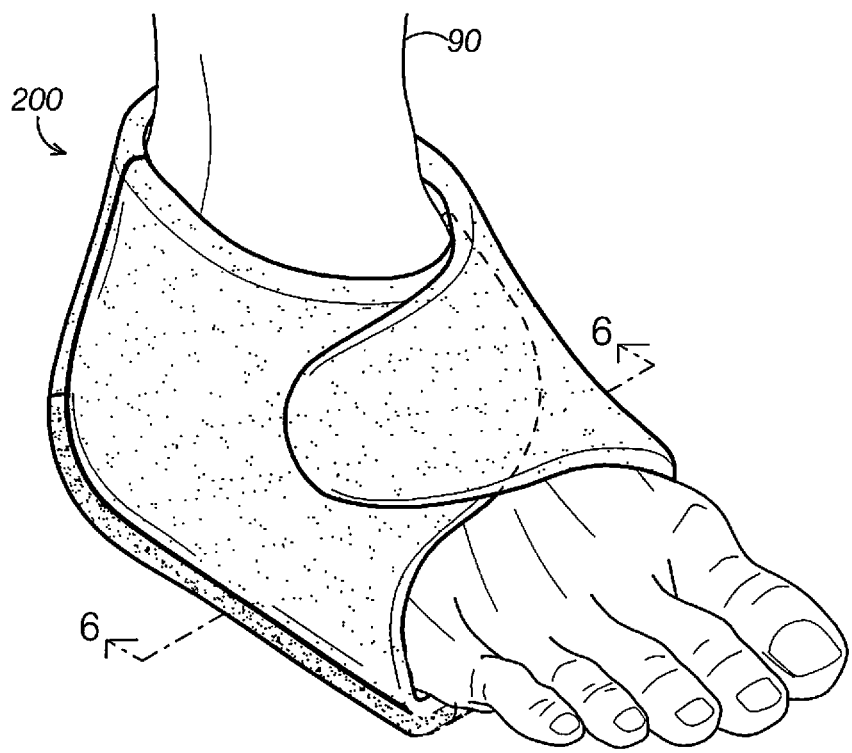
FIG. 5 is a perspective view of a second example of an apparatus for managing pressure on a user's anatomy and/or dressing wounds and injuries.
Figure 6:
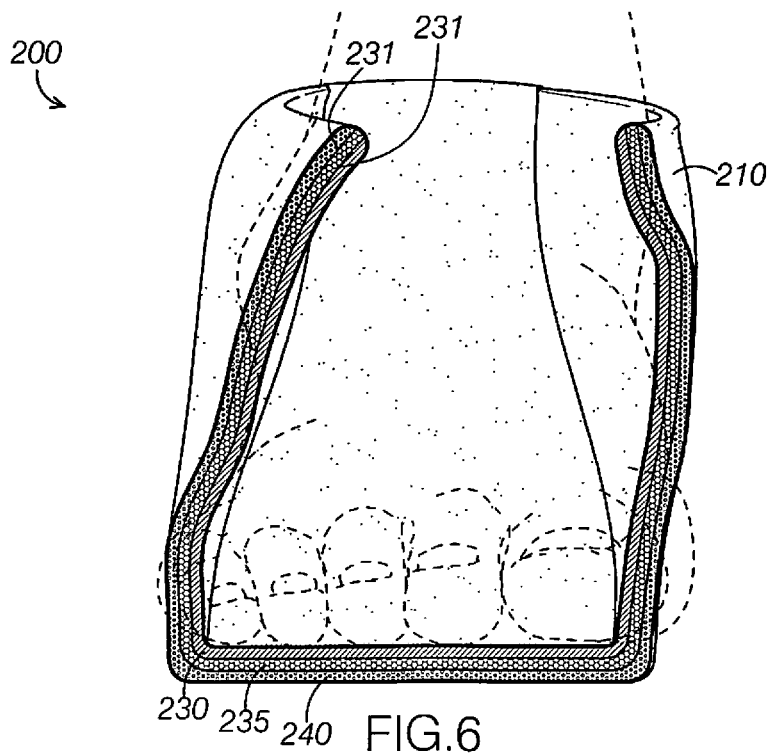
FIG. 6 is a cross-sectional view of the apparatus show in FIG. 5 about the line 6-6.

Turning attention to FIGS. 5 and 6, a second example of an apparatus for managing pressure on users' anatomy and/or dressing wounds and injuries proximate an ankle of user 90, apparatus 200, will now be described. As FIGS. 5 and 6 show, apparatus 200 includes many similar or identical features to apparatus 100 combined in unique and distinct ways. Thus, for the sake of brevity, each feature of apparatus 200 will not be redundantly explained. Rather, key distinctions between apparatus 100 and apparatus 200 will be described in detail and the reader should reference the discussion above for features substantially similar between the two apparatuses.

As FIG. 6 shows, apparatus 200 includes a multi layer wrap 210 substantially similar in many ways to wrap 110. As FIG. 6 shows, however, wrap 210 includes only three layers: a first layer 230 substantially similar to first layer 130, a second layer 235 substantially similar to second layer 135, and a third layer 240 substantially similar to third layer 140. As FIG. 6 illustrates, wrap 210 does not include the fourth layer including a pile material, nor does it include anti-skid layer 170. As a result, apparatus 200 is reduced in thickness, which may make it more easy to adjust and more comfortable to wear. Further, the reduced feature set substantially retains the anatomical contact pressure management features of apparatus 100, thereby providing the core feature set of apparatus 100 in a lower-cost design.

Further, the layers of wrap 210 are interfacially bonded using an adhesive 231. The benefit of using an adhesive was touched on above: adhesive 231 may allow a greater portion of each layer to be extensively interfacially bonded with adjacent layers. More extensive bonding may allow apparatus 200 to apply more consistent level of anatomical pressure across the entirety of its area compared to apparatus 200. Adhesive 231 may, however, be more unreliable than stitching 180 over time, and therefore may degrade in performance more quickly. As a result, both adhesive 231 and stitching 180 provide unique benefits and drawbacks. Some examples may, of course, include both of these fastening/attachment means.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non obvious combinations and subcombinations of the various elements, features, functions and/or properties disclosed above and inherent to those skilled in the art pertaining to such inventions. Where the disclosure or subsequently filed claims recite "a" element, "a first" element such equivalent term, the disclosure or claims should be understood to incorporate one or more such elements, neither requiring, nor excluding two or more such elements.

Applicant(s) reserves the right to subunit claims directed to combinations and subcombinations of the disclosed inventions that are believed to he novel and non-obvious. Inventions embodied in other combinations and subcombinations of features, functions, elements and/or properties may be claimed through amendment of those claims or presentation of new claims in the present application or in a related application. Such amended or new claims, whether they directed to the same invention or a different invention and whether they are different, broader, narrower or equal in scope to the original claims, are to be considered within the subject matter of the inventions described herein.

The invention claimed is:

1. An apparatus to be worn by a user proximate the user's ankle to manage pressure and swelling proximate the ankle, the apparatus comprising:
   a wrap shaped to conform to a portion of a foot and a lower leg of the user and configured to cover and apply pressure to a bandaged area of the user's anatomy proximate the user's ankle, the wrap including:
   multiple layers including at least four compressible layers, at least one of the multiple layers including a compressible foam;
   a first lateral edge and a second lateral edge, the first and second lateral edges defining a channel extending between them, the channel sized to receive a portion of the foot and the lower leg;

a leg portion on a first longitudinal end of the wrap in a position to contact the bandaged area proximate the lower leg; and a foot portion on a second longitudinal end of the wrap opposite the first longitudinal end in a position to contact the bandaged area proximate the foot, the leg portion configured to be flexibly angled from the foot portion;

wherein:

the wrap is configured to be fitted around a portion of the foot and the lower leg to apply a substantially constant anatomical contact pressure to the bandaged area that is great enough to restrict swelling in the bandaged area from fluid accumulating in the bandaged area and is small enough to avoid restricting blood flow through veins in the bandaged area;

the wrap is configured to partially compress the compressible foam and increase the anatomical contact pressure applied to the bandaged area when the second lateral edge of the wrap is pulled toward the first lateral edge of the wrap the compressible foam is pre-compressed substantially throughout the bandaged area to place the compressible foam in a plateau compression condition where it applies a substantially consistent anatomical contact pressure across substantially all of the bandaged area.

2. The apparatus of claim 1, wherein the wrap consists of a single unified structure.

3. The apparatus of claim 2, wherein the multiple layers of the wrap consist of four layers including a soft viscoelastic foam layer and a firm viscoelastic layer that is firmer than the soft viscoelastic layer.

4. The apparatus of claim 3, wherein the multiple layers of the wrap consist of:

an inner, moisture-wicking fabric layer positioned proximate the user's foot when the wrap is fitted around the user's foot;

the soft viscoelastic foam layer interfacially engaged with the moisture-wicking fabric layer adapted to be positioned distal the user's foot;

the firm viscoelastic foam layer interfacially engaged with the soft viscoelastic foam layer adapted to be positioned distal the user's foot; and an outer jacketing fabric layer interfacially engaged with the firm viscoelastic foam layer distal the user's foot.

5. The apparatus of claim 1, wherein the bandaged area includes two ankle regions of the user's anatomy adapted to be postioned proximate the leg portion of the wrap, each ankle region including the user's ankles.

6. The apparatus of claim 1, further comprising stitching routed through at least a portion of each of the multiple layers to retain each of the multiple layers interfacially engaged with each adjacent layer over substantially all of their area.

7. The apparatus of claim 1, wherein the anatomical contact pressure applied across the substantially all of the bandaged area is not less than about 0.3 pounds per square inch and not more than about 0.7 pounds per square inch.

8. An apparatus to be worn by a user proximate the user's ankle to manage pressure and swelling proximate the ankle, the apparatus comprising a wrap shaped to conform to a portion of a foot and a lower leg of the user and configured to cover and apply pressure to a bandaged area of the user's anatomy proximate the user's ankle, the wrap including:

multiple compressible layers, at least one of the multiple layers including a compressible material;

a first lateral edge and a second lateral edge, the first and second lateral edges defining a channel extending between them, the channel sized to receive a portion of the foot and the lower leg;

a leg portion on a first longitudinal end of the wrap in a position to contact the bandaged area proximate the lower leg; and a foot portion on a second longitudinal end of the wrap opposite the first longitudinal end in a position to contact the bandaged area proximate the foot, the leg portion configured to be flexibly angled from the foot portion;

wherein:

the wrap is configured to be fitted around a portion of the foot and the lower leg to consistently apply an anatomical contact pressure to the bandaged area that is great enough to restrict swelling in the bandaged area from fluid accumulating in the bandaged area and is small enough to avoid restricting blood flow through veins in the bandaged area;

the wrap is configured to partially compress the compressible material and increase the anatomical contact pressure applied to the bandaged area when the second lateral edge of the wrap is pulled toward the first lateral edge of the wrap; and the compressible material is pre-compressed substantially throughout the bandaged area to place the compressible material in a plateau compression condition where it applies a substantially consistent anatomical contact pressure across substantially all of the bandaged area.

9. The apparatus of claim 8, wherein the anatomical contact pressure applied across the substantially all of the bandaged area is not less than about 0.3 pounds per square inch and not more than about 0.7 pounds per square inch.

10. The apparatus of claim 8, wherein the wrap consists of a single unified structure.

11. The apparatus of claim 10, wherein the multiple layers of the wrap consist of four layers including a soft viscoelastic foam layer and a firm viscoelastic layer that is firmer than the soft viscoelastic layer.

12. The apparatus of claim 11, wherein the multiple layers of the wrap consist of:

an inner, moisture-wicking fabric layer positioned proximate the user's foot when the wrap is fitted around the user's foot;

the soft viscoelastic foam layer interfacially engaged with the moisture-wicking fabric layer adapted to be positioned distal the user's foot;

the firm viscoelastic foam layer interfacially engaged with the soft viscoelastic foam layer adapted to be positioned distal the user's foot; and an outer jacketing fabric layer interfacially engaged with the firm viscoelastic foam layer adapted to be positioned distal the user's foot.

13. The apparatus of claim 8, wherein the bandaged area includes two ankle regions of the user's anatomy adapted to be positioned proximate the leg portion of the wrap, each ankle region including the user's ankles.

14. The apparatus of claim 8, further comprising stitching routed through at least a portion of each of the multiple layers to retain each of the multiple layers interfacially engaged with each adjacent layer over substantially all of their area.

15. The apparatus of claim 8, wherein the wrap defines a heel depression fitted to conform to a heel of the user.

16. The apparatus of claim 8, wherein the wrap defines a substantially stretchable flap proximate the first lateral edge of the wrap, the flap sized to extend across the channel and the second lateral edge of the wrap when the foot and the lower leg are positioned within the channel.

17. The apparatus of claim 16, further comprising a hook-and-pile connector component stitched to the flap proximate the first lateral edge of the wrap and extending laterally beyond the lateral edge of the wrap, the hook-and-pile connector defining a connecting surface defining a hook region; wherein the multiple layers include an outer pile region configured to engage the hook region of the hook-and-pile connector.

18. The apparatus of claim 8, wherein the wrap defines a base patch interfacially engaged with the wrap proximate the foot portion, the base patch formed of a high-friction, anti-skid material.

19. The apparatus of claim 8, wherein the compressible material is a viscoelastic foam material.

20. The apparatus of claim 19, wherein the viscoelastic foam material takes the form of Confor Foam CF-40 or Confor Foam CF-42 with a thickness between $3/8$-to $5/8$-inches.

* * * * *